United States Patent [19]

Mezrich et al.

[11] 4,131,023
[45] Dec. 26, 1978

[54] PULSE-ECHO ULTRASONIC-IMAGING DISPLAY SYSTEM

[75] Inventors: Reuben S. Mezrich; Charles H. Anderson, both of Rocky Hill, N.J.

[73] Assignee: RCA Corporation, New York, N.Y.

[21] Appl. No.: 766,565

[22] Filed: Feb. 7, 1977

[30] Foreign Application Priority Data

Mar. 4, 1976 [GB] United Kingdom ............... 08661/76
Mar. 4, 1976 [GB] United Kingdom ............... 08663/76

[51] Int. Cl.² ................................................. G01N 29/00
[52] U.S. Cl. ................................................. 73/606; 73/626
[58] Field of Search ............... 73/67.5 R, 67.7, 67.8 R, 73/67.8 S, 67.9, 71.5 US, 606, 607, 625, 614, 632, 626, 641, 642, 629; 340/5 MP, 5 H, 8 FT; 128/2 V, 2.05 Z

[56] References Cited

U.S. PATENT DOCUMENTS

| | | | |
|---|---|---|---|
| 2,700,895 | 2/1955 | Carson | 340/5 MP |
| 2,833,999 | 5/1958 | Howry | 73/642 |
| 3,886,490 | 5/1975 | Green | 340/5 MP |
| 3,895,525 | 7/1975 | Eichelberger et al. | 340/5 MP |
| 3,918,024 | 11/1975 | Macovski | 340/5 MP |
| 3,918,297 | 11/1975 | Rocha | 73/607 |
| 3,937,066 | 2/1976 | Green et al. | 340/5 MP |
| 4,016,750 | 4/1977 | Green | 73/629 |

*Primary Examiner*—Stephen A. Kreitman
*Attorney, Agent, or Firm*—H. Christoffersen; Samuel Cohen; George J. Seligsohn

[57] ABSTRACT

An improvement to a pulse-echo ultrasonic-imaging system employing an acoustic focusing device occupying a fixed aperture to both illuminate internal structure of a visually opaque object with a scanning focused beam of ultrasonic energy and for returning a reflected signal portion of the scanning focused beam passed therethrough for detection. The improvement accomplishes real time scanning by scanning all of the image samples within a group of such samples in a time period not much longer, at most, than the round-trip travel time delay of the focused beam required to receive the reflected signal portion of only a single sample for detection. By way of example, this may be accomplished by a phased-array transducer arrangement.

5 Claims, 8 Drawing Figures

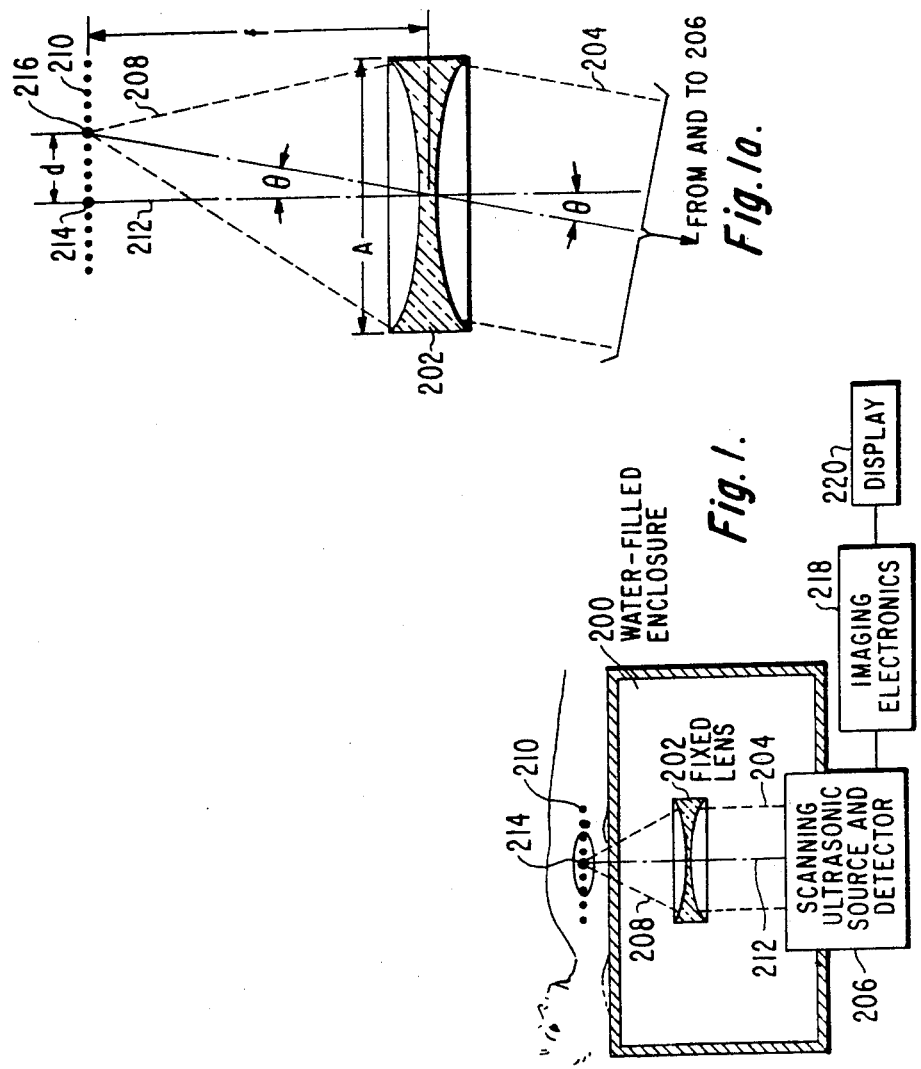

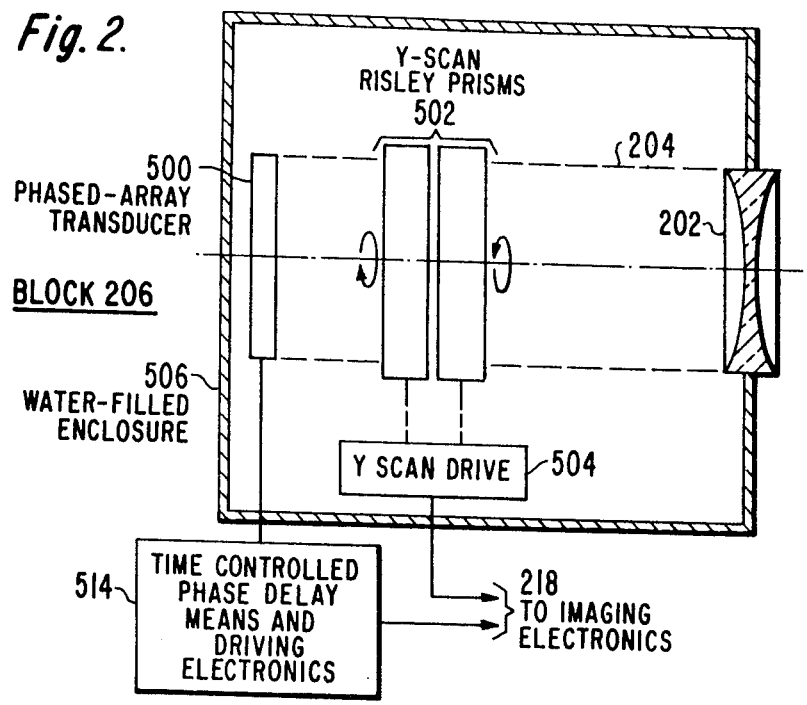
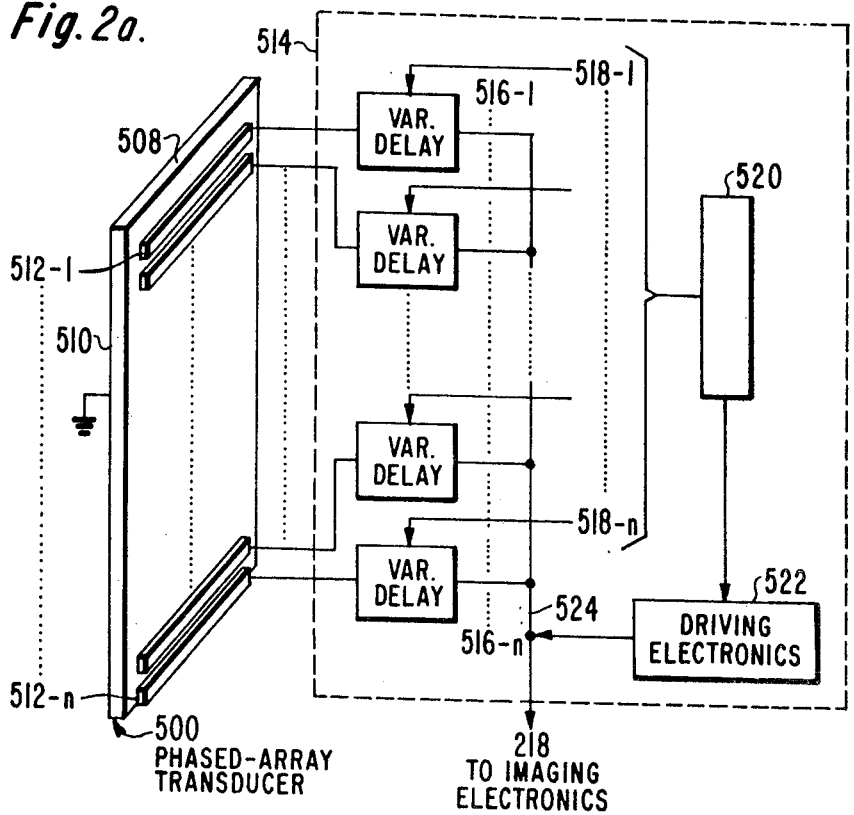

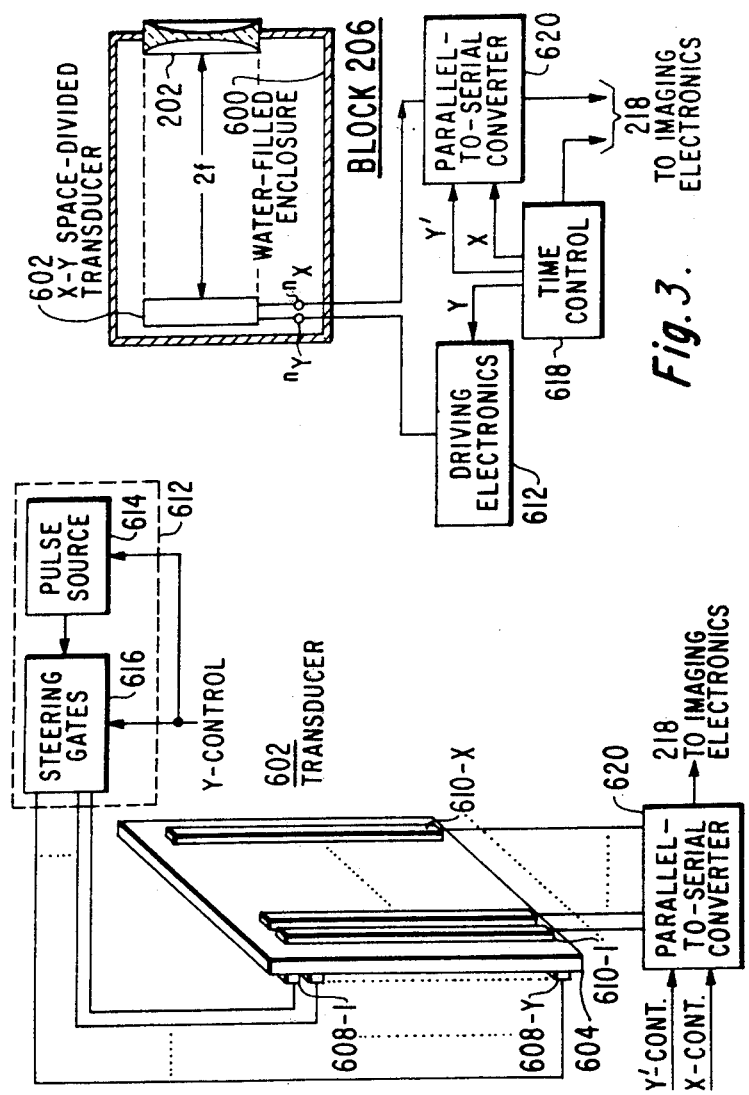

PULSE-ECHO ULTRASONIC-IMAGING DISPLAY SYSTEM

Reference should be made to the following U.S. patent applications, filed concurrently herewith and assigned to the same assignee as the present invention:

Ser. No. 766,564, Mezrich & Koenig
Ser. No. 766,527, Mezrich
Ser. No. 766,528, Mezrich & Vilkomerson
Ser. No. 766,526, Mezrich & Avins The aforesaid U.S. patent application Ser. No. 766,564, Mezrich and Koenig, describes in detail a number of embodiments of a high resolution pulse-echo ultrasonic-imaging display system employing an acoustic focusing device occupying a fixed aperture for both illuminating internal structure of a visually opaque object with a scanning focused beam of ultrasonic energy and for returning a reflected signal portion of the scanning focused beam passed therethrough for detection. The present application, in general, is directed to those certain ones of these embodiments which are employed to provide real time scanning and, in particular, to that embodiment which utilizes phased-array techniques to provide real time scanning.

In the drawings:

FIGS. 1 and 1a generically illustrate the type of pulse-echo ultrasonic-imaging system that may embody the present invention;

FIGS. 2 and 2a illustrate a first species of the scanning and ultrasonic source and detector of FIG. 1 for providing real time scanning;

FIGS. 3 and 3a illustrate a second species of the scanning and ultrasonic source and detector of FIG. 1 for providing real time scanning;

Figure 4:
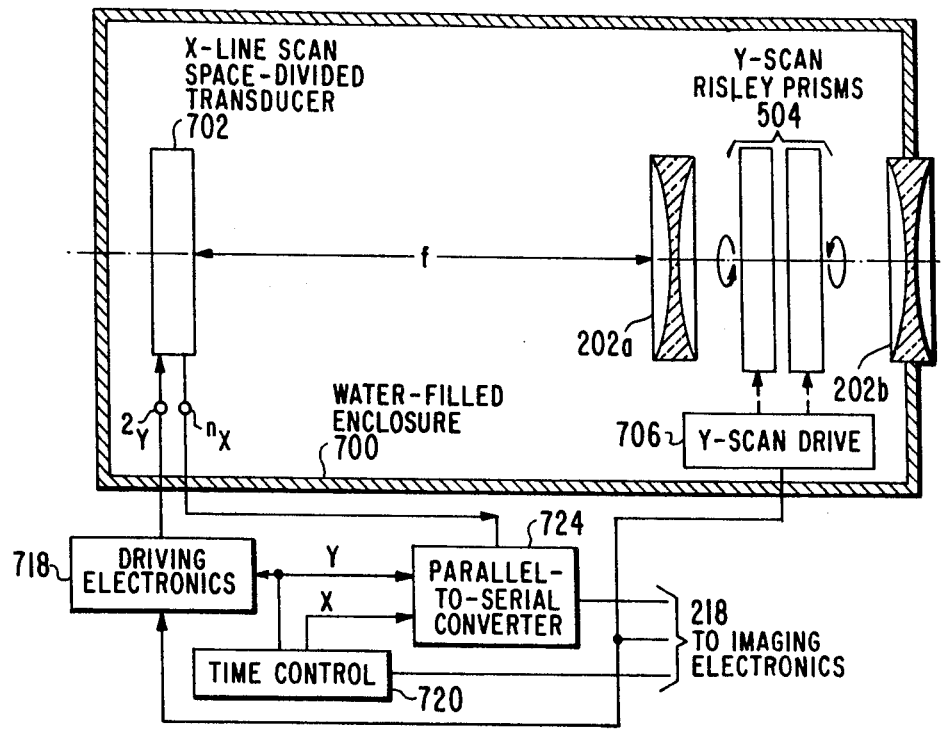
FIGS. 4 and 4a illustrate a third species of the scanning and ultrasonic source and detector of FIG. 1 for providing real time scanning.

FIGS. 1, 1a, 2, 2a, 3, 3a, and 4 and 4a of the present case correspond identically with respective FIGS. 2, 2a, 5, 5a, 6, 6a, 7 and 7a of the aforesaid U.S. patent application Ser. No. 766,564.

Referring now to FIGS. 1 and 1a, there is shown a human patient lying on water-filled table 200. Immersed within water-filled table 200 is fixed lens 202, which is illuminated by a substantially plane wavefront beam 204 of ultrasonic energy from scanning ultrasonic source and detector 206 disposed in space relationship with fixed lens 202.

The term "fixed" lens, as used herein, means that the effective position of the aperture of lens 202 remains substantially stationary with respect to the human patient lying on water-filled table 200 during an image scan. However, in order to select the particular soft tissue within the human patient to be imaged, the operating distance between lens 202 and the human patient may be adjusted, if desired, prior to an image scan, by either changing the height of the top of water-filled table 200 with respect to lens 202 or by changing the position of lens 202 with respect to the top of water-filled table 200, without departing from the above definition of "fixed" lens. Further, since the mere rotation of a circularly symmetrical lens about its own axis has no effect at all on the position of the lens aperture or the way the lens acts on ultrasonic energy transferred therethrough, such mere rotation of the lens about its own axis is to be construed as to be within the above definition of the term "fixed" lens. Fixed lens 202 transfers the ultrasonic energy in plane wavefront beam 204 incident thereon into converging beam 208, which focuses at a small spot of focal plane 210 of lens 202 (located within the body of the human patient).

FIG. 1 shows plane-wafefront illuminating beam 204 of ultrasonic energy at a point in its scan where its direction of travel is parallel to acoustic axis 212 of fixed lens 202. In this case, ultrasonic energy converging beam 208 emerging from fixed lens 202 focuses at a spot centered at focal point 214 in focal plane 210 of lens 202. However, as shown in FIG. 1a, when plane wavefront illuminating beam 204 is at a point in its scan where its direction of travel is angularly displaced by angle $\theta$ from acoustic axis 212 of lens 202, converging beam 208 emerging from lens 202 focuses at a spot centered at point 216 in focal plane 210 of lens 202. As shown in FIG. 1a, point 216 is linearly displaced by a distance d from focal point 214. As is known in the optical art, the relationship between the distance d and the angular displacement $\theta$ is given by the following equation:

$$d = f\theta, \qquad (1)$$

where f is the focal distance of lens 202, as shown in FIG. 1a, and the maximum value of $\theta$ is sufficiently small (as is the case) to be substantially equal in radians to $\tan \theta$.

It will be noted from equation 1 that the value of d varies linearly with $\theta$. Further, as the value $\theta$ varies during a scan, the position of the point, such as point 216, to which beam 208 converges remains in focal plane 210. This ensures a substantially flat-field image (neglecting the effect of any lens aberrations).

Referring now to FIGS. 2 and 2a, there is shown an embodiment of scanning ultrasonic source and detector 206 which employs time division multiplex techniques for achieving real time scanning of the target area. The embodiment of scanning ultrasonic source and detector 206, shown in FIGS. 2 and 2a, comprises x-scan phased-array transducer 500, y-scan Risley prisms 502 and y-scan drive 504 within a water-filled enclosure 506, having lens 202 incorporated in its front wall. X-scan phased array transducer 500, shown in more detail in FIG. 2a, preferably comprises piezoelectric plate 508 having one face thereof covered with grounded electrode 510 and the other face thereof convered with an array of line-section electrodes 512-1 . . . 512-n. Time-controlled phase-delay means and driving electronics 514 supplies exploratory pulses to phased-array transducer 500 and forwards detected echoes and X scan sync signals to imaging electronics 218. Y-scan drive 504 supplies the scan sync signals to imaging electronics 218.

Reference is made to "Microwave Scanning Antennas", Vol. 3, edited by R. C. Hansen, and published by the Academic Press, New York, in 1964, which describes in detail phasedarray techniques, useful in radar. In particular, the direction of the beam of wave energy from a phased-array is a predetermined function of (1) the known distance between adjacent sections of the array, (2) the known velocity of the wave in the propagating medium, and (3) the selectively-controlled difference in phase between the driving wave energy applied to each adjacent pair of array sections. Therefore, phased-array scanning techniques are just as applicable to ultrasonic wave energy as to microwave electromagnetic wave energy.

FIG. 2a shows schematically an embodiment of time-controlled phase-delay means and driving electronics 514. In particular, associated with each line section 512-1 . . . 512-n of phased-array transducer 500 is a corresponding one of signal-controlled bilateral variable delay devices 516-1 . . . 516-n. Each of these variable delay devices effectively inserts an amount of time delay in a signal passing therethrough in accordance with a control signal on the corresponding one of control leads 518-1 . . . 518-n applied thereto from time control 520. Variable delay devices 516-1 . . . 516-n, may be analog devices, such as tapped lines. However, in practice, they would normally be digital devices, such as any of those described in Vol. 3 of the aforesaid "Microwave Scanning Antennas." In operation, driving electronics 522, under the control of time control 520, applies a predetermined number, e.g. 100, exploratory pulses in succession to phased-array transducer 500 through common lead 524 and variable delay devices 516-1 . . . 516-n. Further, time control 520 provides a different set of control signals 518-1 . . . 518-n for each successive exploratory pulse to an appropriately sweep the ultrasonic beam transmitted by transducer 500 in the X direction. The total time of such a sweep should preferably be as short as possible (i.e. the duty cycle of exploratory pulses should be as high as possible) and in no event can be longer than the round-trip travel time to the target area. Thus, if a sweep is composed to 100 exploratory pulses, each having a width of 1 μs and the round trip travel time between the transmission of an exploratory pulse and the receipt of an echo in response thereto is 330 μs (as assumed above), a minimum sweep period with high duty-cycle exploratoy pulses must exceed 100 μs in duration while a maximum sweep period must be less than 330 μs in duration. At the end of a round-trip interval (i.e. 330 μs) variable delay device 516-1 . . . 516-n, under the control of signals 518-1 . . . 518-n from time control 520, again sweep transducer 500 in an identical manner to detect returned echoes and apply the echoes to imaging electronics 218 over common lead 524. Thus, it takes a time interval between one and two times the round trip travel time between the transmission of an exploratory pulse and the return of its responding echo to scan one entire line of the target area in the direction. In more quantitative terms, $$T_X = T_r + T_s \tag{5}$$

$$n_x t < T_s < T_r \tag{6}$$

where $T_X$ is the time to scan a line of the target area in the X direction, $T_r$ is the round trip time, $T_s$ is the sweep period, $n_x$ is the number of sample points in a scan line in the x direction and t is the width of an exploratory pulse. In the assumed example, where $T_r$ is 330 μs, $n_x$ is 100 and t is 1 μs, the value of $T_X$ is greater than 430 μs but less than 660 μs. Further, if a total scan of the target area is composed of 100 lines, a scan period is longer than 43 milliseconds but less than 66 milliseconds (i.e. Y-scan Risley prisms 502 are driven at a rate between approximately 900–1400 rpm). This provides a real time frame rate of between 14 and 24 frames per second.

Referring now to FIGS. 3 and 3a, there is shown a space-divided embodiment of scanning ultrasonic source and detector 206 for providing real-time scanning of the target area. Lens 202 is incorporated into the front wall of water-filled enclosure 600. Immersed in water-filled enclosure 600 is X-Y space-divided transducer 602. Transducer 602 is preferably situated at a distance from lens 202 equal to twice its focal length (2f), as indicated in FIG. 3, so that points on transducer 602 are imaged with unity magnification on a target area plane situated at a distance beyond lens 202 also equal to 2f. Similarly, points in the target area will be imaged with unity magnification at transducer 502. As shown in FIG. 3a, transducer 602 comprises piezoelectric plate 604 having a first set of driving line section electrodes 608-1 . . . 608-y on the left surface thereof and a second set of sensing linesection electrodes 610-1 . . . 610-x on the right face thereof. As shown, the second set of electrodes is orthogonally oriented with respect to the first set of electrodes to thereby define (x · y) cross points therebetween. Each of these cross points corresponds to a sampling point of the target area. If, as has been assumed, x and y both have a value of 100, the total number of sampling points in the scan of the target area is 10,000.

Driving electronics 612 for energizing transducer 602 comprises pulse source 614 and steering gate 616. More specifically, under the control of Y signals from time control 618, steering gate 616 operates as a commutator to selectively supply successive exploratory pulses in sequence to each of driving electrodes 608-1 . . . 608-y, while simultaneously grounding all the non-selected remaining ones of this first set of electrodes. At the time an exploratory pulse is applied to driving electrodes 608-1 . . . 608-y, sensing electrodes 610-1 . . . 610-x are also grounded. This results in a narrow (e.g. 1mm.) line beam of ultrasonic energy consisting of the energy launched from each of the cross-points of the then-selected one of driving electrodes 608-1 . . . 608-y.

Because each sampling point of the target area is imaged at a corresponding cross-point of the transducer in the arrangement of block 206 shown in FIGS. 3, and 3a, the round-trip travel time between the transmission of an exploratory pulse and the receipt of an echo from the target area in response thereto is twice that of the previously-discussed embodiments of block 206. More specifically, if the target area is situated ten inches beyond lens 202 (i.e. 2f = 10 inches), as has been assumed, the total distance between transducer 602 and the target area is 20 inches. Therefore, the round trip travel time is in the order of 660 μs (assuming a velocity of 1500 m/s for the ultrasonic energy in the propagating medium).

Y control signals are applied to pulse source 614 in steering gates 616 at the beginning of a Y repetition period equal to or slightly greater than the round-trip travel time (660 μs) to cause each respective driving electrode 608-1 . . . 608-y to launch an exploratory pulse of ultrasonic energy in consecutive order at substantially 660 μs intervals.

Parallel-to-serial converter 620, which includes a set of x storage elements, a set of input gates under the control of Y' signals from time control 618 for applying the signals sensed by the sensing electrodes 610-1 . . . 610-x to the corresponding storage elements at or near the end of each Y (660 μs) period and a steer-out circuit under the control of x signals from time control 618 for sequentially reading out all the stored signals on the set of storage elements during the following Y period to thereby apply a serial stream of x (e.g. 100) sample point signals to imaging electronics 218 during that Y period. Time control 618 also supplies scan sync signals to imaging electronics 218. Thus, the scan of the entire target area takes (y+1) Y periods or, in the assumed example, 66.66 ms. This is a real-time frame rate of 15 scans of the target area per second.

At the end of any Y period, while parallel-to-serial converter 620 is sampling the echo returned from the target area in response to the exploratory pulse transmitted from a particular one of driving line-section electrodes at the beginning of that Y period, it may be desirable for steering gate 616 to momentarily disconnect electrodes 608-1 ... 608-y (i.e. allow electrode 608-1 ... 608-y to float), in order to reduce the effective shunting parasitic load impedance between sensing electrodes 610-1 ... 610-x and ground. This shunting load impedance tends to reduce the effective sensitivity and raise the effective signal-to-noise ratio of the sensed signals forwarded by sensing electrodes 610-1 ... 610-x to the storage elements of parallel-to-serial converter 620. In any event, all other things being equal, the greater the number x-y cross-points, the greater is the effect of the shunting load impedance.

Figure 4A:
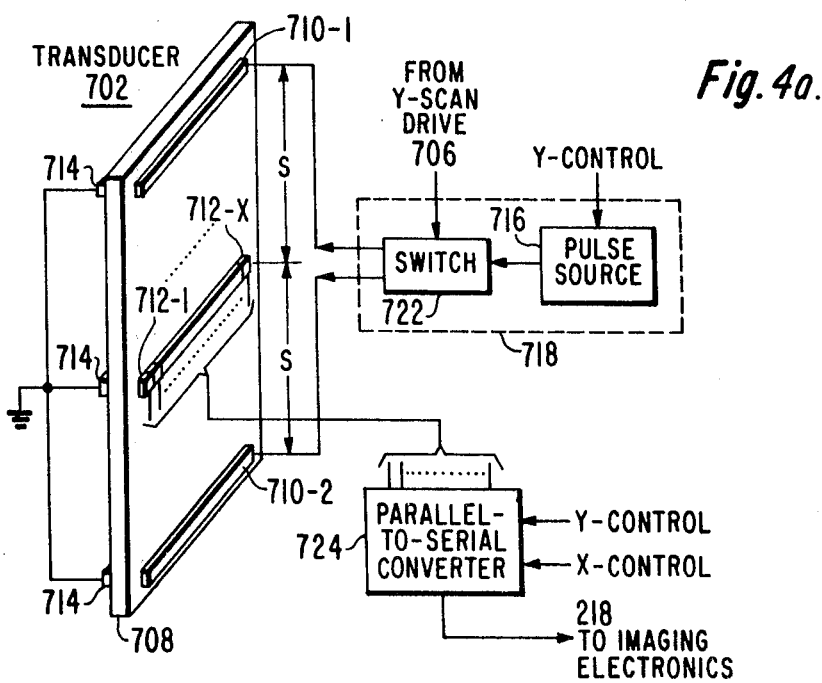

FIGS. 4 and 4a show an embodiment of scanning ultrasonic source and detector 206, which operationally is the functional equivalent of the embodiment shown in FIGS. 3 and 3a, but which inherently exhibits a much lower parasitic shunting load impedance.

Referring to FIG. 4, immersed in water-filled enclosure 700 are X-line-scan space-divided transducer 702 and Y-scan Risley prisms 704 coupled to Y-scan drive 706. Sample points of the target area are imaged at corresponding points of transducer 702 by a lens system composed of two spaced lenses 202a and 202b, situated, as shown, on either side of Y-scan Risley prisms 704. This imaging results from the fact that lens 202b, which is incorporated in the front wall of water-filled enclosure 700, has its focal plane situated in coincidence with the target area, and transducer 702 is located in the focal plane of lens 202a. The use of a two-lens system to provide imaging of the sample points of the target area on transducer 702 is to be preferred in the arrangement of FIG. 4 to the single lens approach used in FIG. 2 because the two-lens approach ensures less distortion because the Y-scan Risley prisms are illuminated with paraxial plane-wave acoustic energy, rather than spherical wave energy from a linearly-scanned point source.

Referring now to FIG. 4a, transducer 702 comprises piezoelectric plage 708 having two driving line-section electrodes 710-1 and 710-2 mounted on the right face thereof. Halfway between driving line-section electrode 710-1 and 710-2, at a distance "s" from each, is a linear array of individual sensing electrodes 712-1 ... 712-x. Mounted on the left face of piezoelectric plate 708, in corresponding relationship with each of driving linesection electrodes 710-1 and 710-2 and the linear array of sensing electrodes 712-1 ... 712-x are grounded linesection electrodes 714, as shown. Pulse source 716 of driving electronics 718, in response to Y control signals from time control 720, applies a series of exploratory pulses to a selected one of driving electrodes 710-1 and 710-2 through switch 722 at a repetition rate which is substantially equal to the round trip travel time between the transmission of an exploratory pulse and a receipt of an echo from the target area response thereto (e.g. 660 μm). Switch 722 selects the one of the driving electrodes 710-1 and 710-2 which an exploratory pulse is forwarded in response to a control signal from Y-scan drive 706 applied thereto.

Y-scan Risley prism 704 are continuously rotating during the time an exploratory-pulse is traveling toward the target and during the time that an echo therefrom is traveling back toward transducer 702. Therefore, an echo responsive to an exploratory pulse launched from a selected one of driving electrodes 710-1 and 710-2 does not return to that selected driving electrode, but is incrementally deflected in the Y direction by a given distance which is determined by the speed of rotation of Y-scan Risley prism 704 and the round-trip travel time to the target area. The spacing distance between the linear array of sensing electrode 712-1 ... 712-x and either one of the driving electrode 710-1 and 710-2 is chosen to be equal to this given distance. Furthermore, during a first half of each cycle of Y-scan Risley prism 704, a beam of acoustic energy passing therethrough is deflected in the Y-direction from top-to-bottom. However, during the remaining half of each cycle of location of Y-scan Risley prism 704, a beam of acoustic energy passing therethrough is deflected in the Y-direction from bottom-to-top. The control signal applied to switch 722 from Y-scan drive 706 causes exploratory pulses to be forwarded to driving electrode 710-1 and driving electrode 710-2 to be grouned during the half-cycle of rotation of Y-scan Risley prism 704 when the acoustic beam is being deflected from top-to-bottom. Similarly, exploratory pulses are applied to driving electrode 710-2 and driving electrode 710-1 is grounded by switch 722 during those half-cycles of Risley prism 704 during which the acoustic beam is deflected from bottom-to-top. In either case, returning echoes from the target area are incident on the linear-array of sensing electrode 712-1 ... 712-x.

Assuming that the cycle period of Y-scan Risley prism 704 is not exactly equal to an even integral multiple of the repetition period of the exploratory pulses, a different set of X-lines of the target area will be sampled during consecutive half-cycles of rotation of Risley prism 704. That is, an inter-laced raster scan of the target area is achieved.

Parallel-to-serial converter 724, which is structurally and functionally identical to parallel-to-serial converter 620, described above, the end of each Y period (i.e. exploratory pulse repetition period) samples in parallel and stores all the line of target area echo signals then being received by sensing electrode 712-1 ... 712-x, and then converts the stored signals into a corresponding serial stream during the following Y periods.

What is claimed is:

1. In apparatus for use in an ultrasonic pulse-echo system capable of displaying an image of certain internal structure of a visually opaque object being scanned with ultrasonic wave energy, said apparatus including an acoustic focusing device occupying a given aperture which aperture remains substantially fixed in position with respect to said object while said object is being scanned, and ultrasonic beam forming means including transducer means generating successive pulses of ultrasonic wave energy and beam scanning means for illuminating said certain internal structure through said focusing device with a scanning focused beam of said pulsed ultrasonic wave energy, said transducer means being situated remotely from both said focusing device and from said internal structure for receiving and detecting a signal portion of said focused beam relfected from said certain internal structure and returned through said focusing device to said transducer means after a time delay proportional to the distance between said remotely situated transducer means and internal structure; the improvement:

wherein said system displays said image of said certain internal structure in at least one frame, a frame comprising a first plurality of groups of image samples, each of said groups containing a second plurality of individual image sampls, and wherein said beam scanning means comprises means for scanning an entire individual group of image samples in a first time period no greater than said time delay, whereby respective signal portions of said focused beam corresponding to all said second plurality of individual image samples of any of said groups can be received and detected within the duration of a second time period equal to the sum of said first time period and said time delay and a frame can be displayed in a third time period equal to said first plurality of said second time periods.

2. The apparatus defined in claim 1, wherein said scanning means includes means operative during each frame for scanning said focused beam in an X-Y raster format consisting of a plurality of substantially parallel scan lines equal to said first plurality, each scan line extending substantially linearly in a first direction and corresponding to an individual one of said groups, said parallel scan lines being arranged with respect to each other in a second direction which is substantially orthogonal to said first direction.

3. The apparatus defined in claim 1, wherein said scanning means includes a given distribution of spaced electrodes in cooperative relationship with said transducer means for controlling the scanning of said focused beam in at least one of said first and second directions in accordance with the energization of said respective spaced electrodes, and means for controlling the energization of said respective spaced electrodes.

4. The apparatus defined in claim 3, wherein said distribution of spaced electrodes constitutes a phased array and wherein said beam scanning means includes a variable phase delay means coupled to said respective spaced electrodes, first means operative solely during a first-occurring portion of every second time period of a frame for supplying relatively phase delayed driving pulses to said respective spaced electrodes through said variable phase delay means, said firstoccurring portion being equal in length to said first time period, to thereby cause said focused beam to scan through a scan line of said frame within a first time period, and second means operative during a secnd-occurring portion of every second time period in which a signal portion associated with said scan line is being received and detected for deriving an output from said spaced electrodes through said variable phase delay means.

5. The apparatus defined in claim 4, wherein said scanning means further includes a pair of Risley prisms for controlling said scan in said second direction.

* * * * *

UNITED STATES PATENT AND TRADEMARK OFFICE
CERTIFICATE OF CORRECTION

PATENT NO.   : 4,131,023
DATED        : December 26, 1978
INVENTOR(S)  : Reuben Saul Mezrich et al.

It is certified that error appears in the above-identified patent and that said Letters Patent is hereby corrected as shown below:

Column 2, line 7, "wafefront" should read --wavefront--

Column 2, line 60, "phasedarray" should read --phased-array--
Column 4, line 8, "502" should read --602--
Column 4, line 12, "linesection" should read --line-section--

Column 5, line 53, "linesection" should read --line-section--
Column 5, line 55, "linesection" should read --line-section--
Column 6, line 64, "relfected" should read --reflected--
Column 7, line 6, "sampls" should read --samples--
Column 8, line 17 "firstoccurring" should read --first-occurring--
Column 8, line 21, "secnd" should read --second--

Signed and Sealed this

First Day of May 1979

[SEAL]

Attest:

RUTH C. MASON
Attesting Officer

DONALD W. BANNER
Commissioner of Patents and Trademarks